United States Patent
Lowe et al.

(10) Patent No.: US 8,907,117 B2
(45) Date of Patent: Dec. 9, 2014

(54) ANTI-TUMOR AND ANTI-INFLAMMATORY DICINNAMOYL-GLYCEROL ESTERS AND THEIR ANALOGUES

(76) Inventors: Henry Lowe, Kingston (JM); Joseph L. Bryant, Baltimore, MD (US)

( * ) Notice: Subject to any disclaimer, the term of this patent is extended or adjusted under 35 U.S.C. 154(b) by 0 days.

(21) Appl. No.: 13/608,599

(22) Filed: Sep. 10, 2012

(65) Prior Publication Data
US 2013/0210913 A1 Aug. 15, 2013

Related U.S. Application Data

(60) Provisional application No. 61/532,267, filed on Sep. 8, 2011.

(51) Int. Cl.
| | |
|---|---|
| C07C 67/293 | (2006.01) |
| C07C 69/734 | (2006.01) |
| C07C 69/618 | (2006.01) |
| C07C 67/08 | (2006.01) |
| C07C 67/26 | (2006.01) |
| C07C 67/297 | (2006.01) |
| C07C 67/343 | (2006.01) |

(52) U.S. Cl.
CPC .............. *C07C 69/618* (2013.01); *C07C 67/08* (2013.01); *C07C 67/26* (2013.01); *C07C 67/297* (2013.01); *C07C 67/343* (2013.01)
USPC ............................................. 560/75; 514/533

(58) Field of Classification Search
CPC combination set(s) only.
See application file for complete search history.

(56) References Cited

U.S. PATENT DOCUMENTS

| | | | |
|---|---|---|---|
| 7,713,556 B2 | 5/2010 | Lowe | |
| 2009/0136566 A1* | 5/2009 | Krasutsky et al. | 424/450 |

FOREIGN PATENT DOCUMENTS

| | | | | |
|---|---|---|---|---|
| CA | 2715662 | * | 12/2010 | C07D 303/16 |

* cited by examiner

*Primary Examiner* — Jafar Parsa
*Assistant Examiner* — Amy C Bonaparte
(74) *Attorney, Agent, or Firm* — Ober, Kaler, Grimes & Shriver; Royal W. Craig

(57) ABSTRACT

Synthetic dicinnamate compounds and their analogs are disclosed that exhibit anti-tumor activity and/or an anti-inflammatory activity, and have beneficial activity principally in destroying cancer cells. Furthermore, methods for the extraction of the extracts are disclosed.

1 Claim, 4 Drawing Sheets

*Synthesis Route for the Novel Synthesis of Figure 1*

(E)-3-(cinnamoyloxy)-2-hydroxypropyl 3-(3,4-dimethoxyphenyl)acrylate (E)-3-(cinnamoyloxy)-2-hydroxypropyl 3-(3,4-dihydroxyphenyl)acrylate 2-acetoxy-4-((E)-3-(3-((E)-3-(3,4-dimethoxyphenyl)acryloyloxy)-2-hydroxypropoxy)-3-oxoprop-1-enyl)benzoic acid Acetylation of 4-Formyl-2-Hydroxybenzoic Acid

US 8,907,117 B2

ANTI-TUMOR AND ANTI-INFLAMMATORY DICINNAMOYL-GLYCEROL ESTERS AND THEIR ANALOGUES

CROSS-REFERENCE TO RELATED APPLICATIONS

The present invention derives priority from U.S. provisional application Ser. No. 61/532,267 filed Sep. 8, 2011.

BACKGROUND OF THE INVENTION

1. Field of the Invention

The present invention relates to anti-cancer drug and, more particularly, to synthetic dicinnamate compounds and their analogues that exhibit anti-tumor activity and/or an anti-inflammatory activity, that has beneficial activity principally in destroying cancer cells.

2. Description of the Background

There is great growth in the overlapping fields of biology, technology, and medicine, including remarkable advances in cellular biology that have given a new understanding of the molecular basis for some diseases. Nevertheless, the incidence of some forms of cancer continues to rise. This is particularly true of breast cancer, a leading cause of death in women. Considerable effort has focused on the early detection of cellular transformation and tumor formation in breast tissue.

The increased focus on cellular biology has led to a profusion of drugs to treat cancer patients. These drugs include alkylating agents, intercalating agents, antimetabolites, etc., most of which target DNA or enzymes regulating the DNA duplication and elongation process. However, rapidly growing tumors do not always exhibit high levels of cell proliferation, but may also exhibit low levels of cell death compared to the normal cell population from which these tumor cells issue, For these types of rapidly growing tumors, the mentioned drugs are not effective. In addition, the great majority of the drugs currently available for treatment of cancer are toxic and involve detrimental side-effects on healthy cells, tissues and organs.

The high-technology approach obfuscated many promising therapeutic drugs derived from natural origins. A successful anticancer drug should kill or incapacitate cancer cells without causing excessive damage to normal cells. This ideal situation is achievable by inducing apoptosis in cancer cells without undue side effects, and organic drugs are well-suited. Apoptosis is a programmed cell death initiated by the nucleus. Apoptosis is a mechanism of cell death that incurs little or no inflammatory response. Currently, radiation is effective in producing cell death by apoptosis but is dependent on dose rate as well as ionization density, and this subjects other non-tumor cells to radiation risks.

Natural products are the most consistently successful source of drug leads. However, natural products inherently depend on availability of scarce resources. Indeed, certain natural drugs are derived from rare and/or exotic plants and this can severely curtail the supply. It is very common, therefore, for scientists to attempt to isolate and synthesize the active component(s) of such rare natural drugs. For example, in his U.S. Pat. No. 7,713,556 issued May 11, 2010, the present inventor disclosed methods of treating cancer by administering a composition comprising and extract of Jamaican Ball Moss (*Tillandsia recurvata*) in a therapeutic compound. Jamaican Ball Moss is not found in abundance, and not at all outside Jamaica, and as described herein the present inventor has devoted significant subsequent effort to isolating the active compound and synthesizing it.

SUMMARY OF THE INVENTION

It is, therefore, the primary object of the present invention to provide a synthetic therapeutic drug based on natural extracts that kills cancerous tumor cells by apoptosis.

It is another object to provide an anti-cancerous therapeutic drag as above, comprising a synthase of active therapeutic compounds derived from the indigenous Jamaican Ball Moss plant (*Tillandsia Recurvata*).

It is another object to provide an anti-cancerous therapeutic drug comprising glycerol esters and their analogues.

The present invention is a synthetic therapeutic drug chosen from among the group comprising:

1) (E)-3-(cinnamoyloxy)-2-hydroxypropyl 3-(3,4-dimethoxyphenyl)acrylate ["dimethoxy-dicinnamate"]

2) (E)-3-(cinnamoyloxy)-2-hydroxypropyl 3-(3,4-dihydroxyphenyl)acrylate ["dihydroxy-dicinnamate"]

3) 2-acetoxy-4-((E)-3-(3-((E)-3-(3,4-dimethoxyphenyl)acryloyloxy)-2-hydroxypropoxy)-3-oxoprop-1-enyl)benzoic acid.

The present invention also includes the method of synthesizing the foregoing. In all cases the synthase may be used as an anti-cancer drug with possibly other therapeutic uses (i.e. anti-inflammatory), and a high-level of efficacy has been shown by positive test results.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention is a group of synthetic dicinnamate compounds and their analogues that exhibit anti-tumor activity and/or an anti-inflammatory activity, that have beneficial activity principally in destroying cancer cells. The dicinnamate compounds are synthetic version of an isolated extract of plant biomass. Specifically, in his U.S. Pat. No. 7,713,556 issued May 11, 2010 the present inventor established an anti-tumor activity and/or an anti-inflammatory activity in the indigenous Jamaican plant Ball Moss (*Tillandsia recurvata*). In accordance with the present invention the dicinnamate molecule and its analogs were synthesized, their chemical nature was determined, and their anti-cancer bioactivity was established by potent in vitro and in vivo anti-cancer test results on several different refractory cancer cell lines.

Isolation

Figure 1:
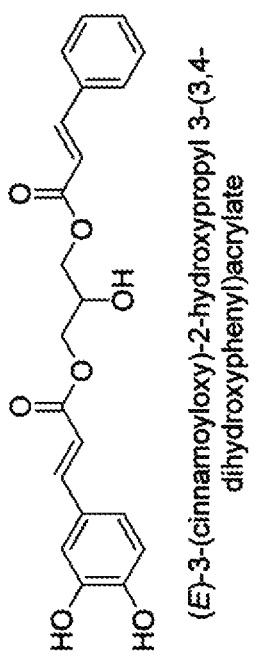
FIG. 1 shows the chemical structure of the synthesized dimethoxy-dicinnamate analog of the present invention.
Figure 2:
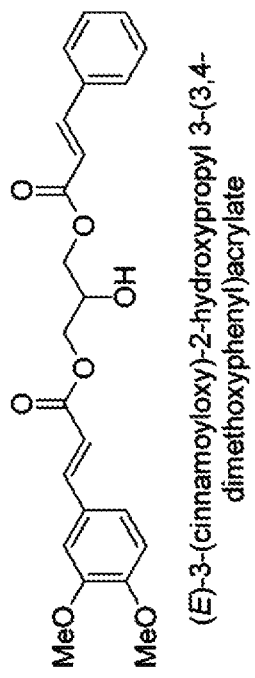
FIG. 2 shows the chemical structure of the synthesized dihydroxy-dicinnamate analog of the present invention.
Figure 3:
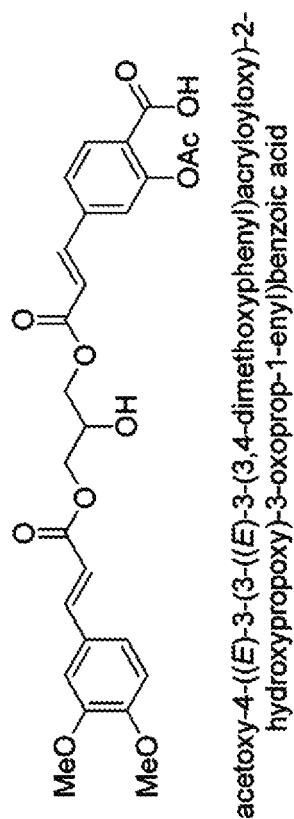
FIG. 3 shows the chemical structure of the synthesized di-acetoxy/benzoic acid analog of the present invention.

*Tillandsia recurvate* (Jamaican Ball Moss) was subjected to conventional drying techniques such as convective drying, sun drying, room air drying and solar drying (using polythene tent dryer), and the dried specimen was milled. The milled specimen was mixed with either a halogenated hydrocarbon solvent such as chloroform, or an alcohol solvent such as methanol, and the methanol extract and chloroform extracts were filtered and subjected to NMR spectroscopic analysis. The presence of a dicinnamate molecule, specifically 1,3-di-O-cinnamoyl glycerol, (E)-3-(cinnamoyloxy)-2-hydroxypropyl 3-(3,4-dimethoxyphenyl)acrylate), and ethyl caffeiate were detected in both methanol and chloroform extracts. In accordance with the present invention the dicinnamate molecule and its analogs were synthesized, their chemical nature was determined, and their anti-cancer bio-activity was established. The synthesis of three dicinnamate compounds, FIGS. 1-3 was completed successfully as described below. The three synthetic dicinnamate compound analogs are shown in FIGS. 1-3 and include:

1) (E)-3-(cinnamoyloxy)-2-hydroxypropyl 3-(3,4-dimethoxyphenyl)acrylate ["dimethoxy-dicinnamate];

2) (E)-3-(cinnamoyloxy)-2-hydroxypropyl 3-(3,4-dihydroxyphenyl)acrylate ["dihydroxy-dicinnamate]

3) 2-acetoxy-4-((E)-3-(3-((E)-3-(3,4-dimethoxyphenyl)acryloyloxy)-2-hydroxypropoxy)-3-oxoprop-1-enyl)benzoic acid.

Synthesis

Conventional synthesis procedures for the analogs shown in FIGS. 2 and 3 were ineffective due to the complex reaction mixtures, and so a novel synthesis procedure was developed for all three analogs. The generalized steps are as follows:

1$^{st}$: produce appropriate ylide; and

2d: couple the ylide with the appropriate aldehyde.

Figure 4:
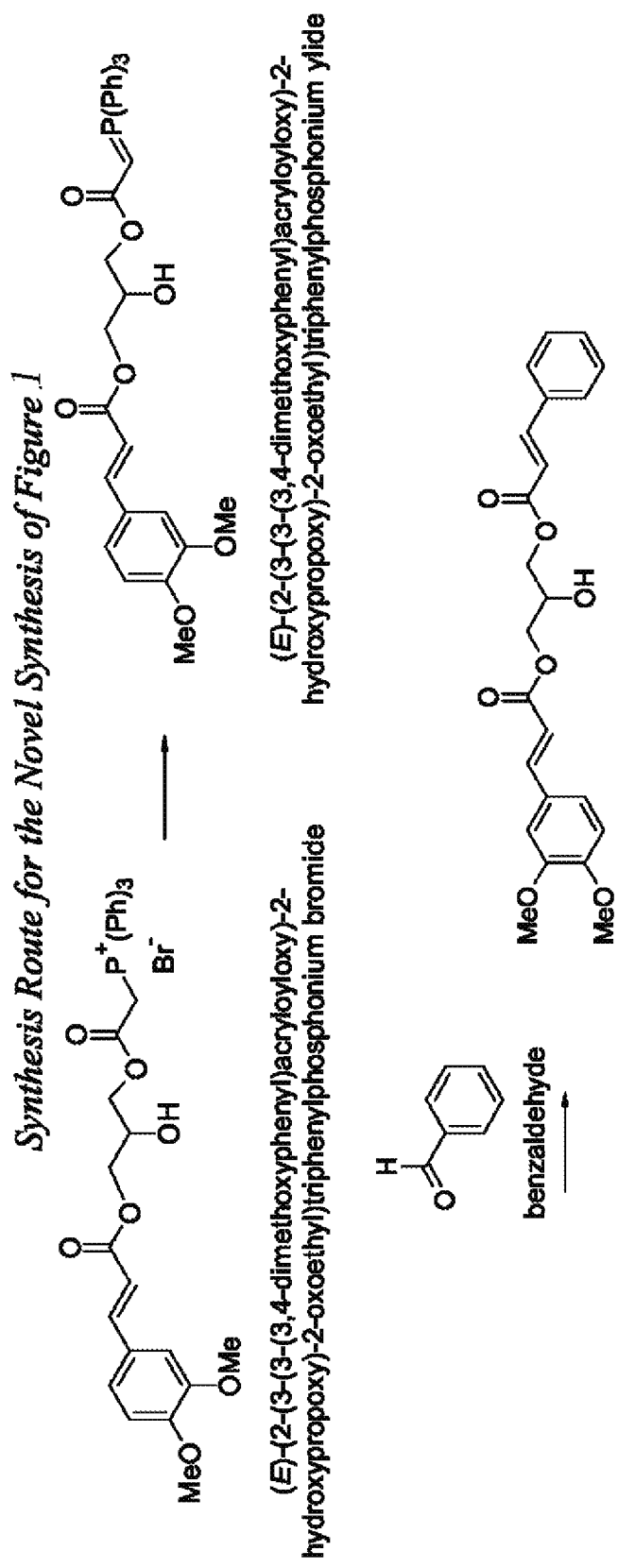
FIG. 4 shows the synthetic reaction scheme for the analog of FIG. 1.

For the analog of FIG. 1, the first step involves taking phosphonium bromide and chemically producing the triphenyl phosphonium ylide. The second step relies on a Wittig reaction, a lesser-known reaction used in organic synthesis for the preparation of alkenes. A Wittig reagent (aldehyde) is reacted with the triphenyl phosphonium ylide to give an alkene and triphenylphosphine oxide. The third step is joining the two key components together. Specifically, the steps are:

1$^{st}$: synthesis of phosphonium bromide ((E)-(2-(3-(3-(3,4-dimethoxyphenyl)acryloyloxy)-2-hydroxypropoxy)-2-oxoethyl)triphenylphosphonium bromide);

2d: convert phosphonium bromide to appropriate triphenyl phosphonium ylide (i.e. (E)-(2-(3-(3-(3,4-dimethoxyphenyl)acryloyloxy)-2-hydroxypropoxy)-2-oxoethyl)triphenylphosphonium ylide);

3$^{rd}$: couple the ylide with the appropriate aldehyde (benzaldehyde);

The reaction scheme for the analog of FIG. 1 is shown graphically in FIG. 4, with the end result of (E)-2-hydroxy-3-((E)-3-p-tolylacryloyloxy)propyl 3-(3,4-dimethoxyphenyl)acrylate. The reaction scheme of FIG. 4 was demonstrated on a 250 mg scale and the identity of the product was confirmed using liquid chromatography-mass spectrometry (LC/MS) and observing the ion for the sodium adduct of the parent molecular ion: [M+Na]=435. The mass spectrometer was operated in positive ion mode.

Figure 5:
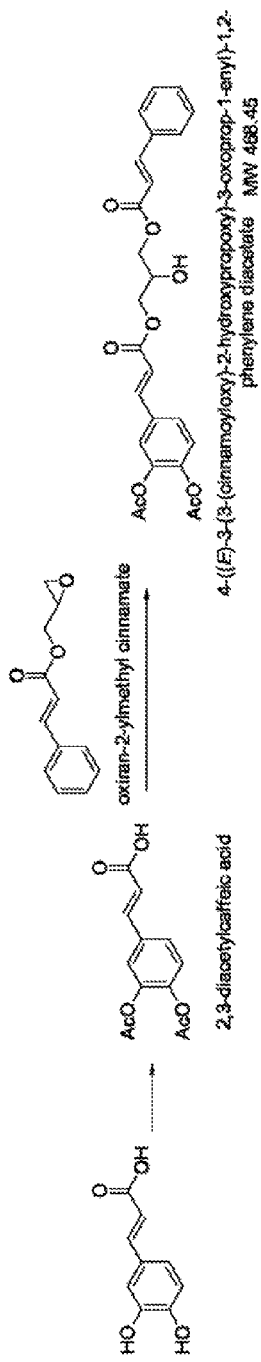
FIG. 5 shows the synthetic reaction scheme for the analog of FIG. 2.
Figure 6:
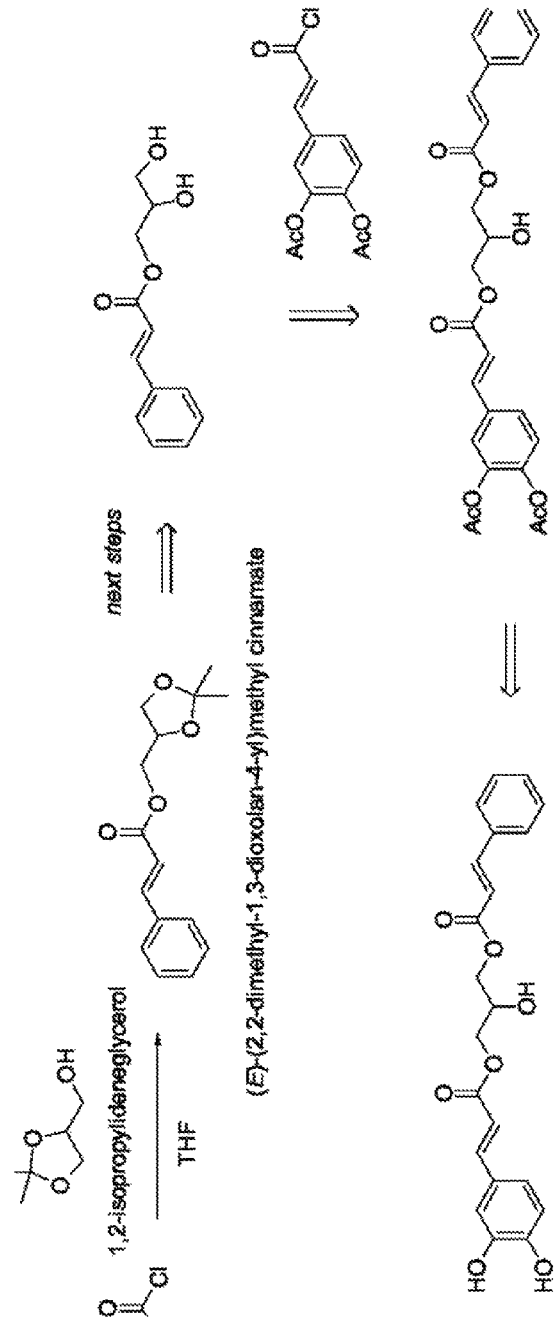
FIG. 6 shows an alternative synthetic reaction scheme for the analog of FIG. 2.

The analog of FIG. 2 may be synthesized from suitably protected caffeic acid. This synthesis strategy is shown in FIG. 5. Caffeic acid is treated with acetic anhydride to give 2,3-diacetyl caffeic acid. The glycerol backbone is then formed by way of oxiran-2-ylmethyl cinnamate. In practice several attempts were made varying the molar ratio of 2,3-diacetylcaffeic acid to oxiran-2-ylmethyl cinnamate within a range of from 2.5:1 to 1.5:1 to 1:1. In all instances, desired product was detected using LC/MS. Identity was based on an ion of 407 which is consistent for loss of a proton under negative ionization electrospray conditions employed in the mass spectrometer. An alternative approach to the analog of FIG. 2 may use the reaction scheme of FIG. 6.

Finally, the analog of FIG. 3 exhibits a lack of symmetry and additional functionality in the acetyl salicyclic acid portion and this necessitates a different synthetic approach. The literature is replete with methods for synthesizing diglycerides, but most of these procedures use benzyl groups in the synthesis followed by hydrogenation which route would not work for the compound of FIG. 3. Again the use of Wittig chemistry is the preferred approach to forming the double bond linkage to a glycerol back bone. Specifically, the novel synthesis procedure entails the following generalized steps:

1$^{st}$: produce appropriate ylide; and

Figure 7:
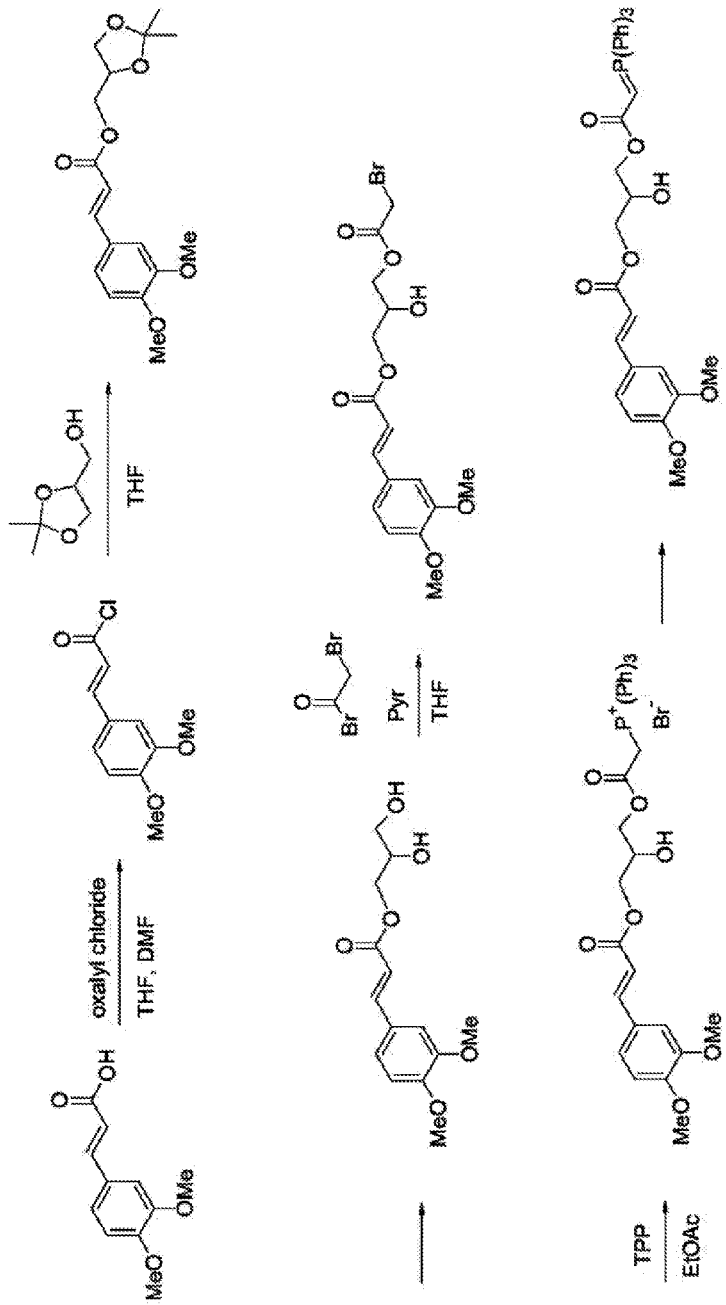
FIG. 7 shows the synthetic reaction scheme for the analog of FIG. 3.
Figure 8:
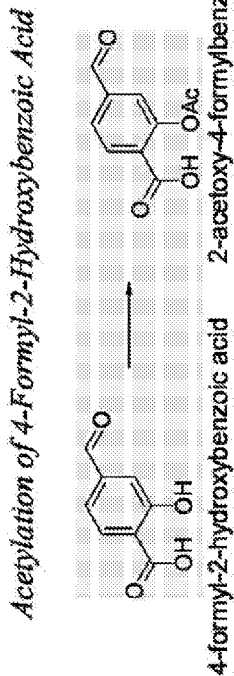
FIG. 8 illustrates the acetylation reaction for the analog of FIG. 3.

2d: couple the ylide with the appropriate aldehyde,

The specific reaction scheme is shown in FIG. 7. 3,4-Dimethoxycaffeic acid was converted to the corresponding acid chloride using standard conditions. The acid chloride was then attached to 1,2-isoprpylideneglycerol to establish one side of the molecule. The isopropylidene group was removed under acidic conditions which reveal the terminal hydroxyl group for coupling to bromoacetyl bromide. Triphenyphosphine gave the corresponding phosphonium bromide which was converted the ylide necessary for the Wittig coupling. The other half of molecule came from 4-Formyl-2-hydroxybenzoic acid. This compound called for acetylation of 4-Formyl-2-Hydroxybenzoic Acid under standard conditions, as illustrated in FIG. 8. A coupling with 2-formyl-5-hydroxybenzoic acid was also attempted. In this case running the reaction with acetic anhydride ($AC_2O$) and triethylamine (TEA) at reflux successfully drove the reaction to completion. Reaction between the 2-acetoxy-5-formylbenzoic acid and a 5-formyl-2-hydroxybenzoic acid ylide went smoothly to yield FIG. 3.

Test Results

The biomass equivalents of FIGS. 1-3 were tested in vitro against the potent melanoma B-16 cell lines utilizing the extremely sensitive 3H thymidine incorporation in vitro. The results are encouraging, with similar efficacy as a number of clinically proven anticancer agents including Paclitaxel (Taxol®), isolated from the bark of the Pacific Yew tree. One skilled in the art should understand that further studies should be conducted including in vitro ADME/TOX (adsorption, distribution, metabolism, elimination and toxicity) studies; cancer cell line selectivity in vitro studies; in vivo animal efficacy and toxicity studies; in vivo pharmacokinetic studies; both in vitro and in vivo mechanism of action (MOA) studies; structure-activity relationship (SAR) studies; and medicinal chemistry studies, all of which should further improve efficacy and reduce toxicity of the synthetic compounds to improve the therapeutic index.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A method for the synthesis of (E)-3-(cinnamoyloxy)-2-hydroxypropyl 3-(3,4-dimethoxyphenyl)acrylate comprising the steps of:
   i) providing a first reactant comprising phosphonium bromide [((E)-(2-(3-(3-(3,4-dimethoxyphenyl)acryloyloxy)-2-hydroxypropoxy)-2-oxoethyl)triphenylphosphonium bromide)];
   ii) converting said first reactant to a triphenyl phosphonium ylide [(E)-(2-(3-(3-(3,4-dimethoxyphenyl)acryloyloxy)-2-hydroxypropoxy)-2-oxoethyl)triphenylphosphonium ylide];
   iii) providing a second reactant comprising benzaldehyde;
   iv) reacting the triphenyl phosphonium ylide provided in step ii) with the second reactant provided in step iv) to form one or more covalent bond(s) coupling said triphenyl phosphonium ylide with the second reactant to yield a dimethoxydicinnamate compound of the formula (E)-3-(cinnamoyloxy)-2-hydroxypropyl 3-(3,4-dimethoxyphenyl)acrylate.

* * * * *